(12) United States Patent
McKay

(10) Patent No.: US 7,998,207 B2
(45) Date of Patent: Aug. 16, 2011

(54) SYNTHETIC REINFORCED INTERBODY FUSION IMPLANTS

(75) Inventor: William F. McKay, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1327 days.

(21) Appl. No.: 11/179,325

(22) Filed: Jul. 12, 2005

(65) Prior Publication Data

US 2006/0025861 A1 Feb. 2, 2006

Related U.S. Application Data

(63) Continuation of application No. 10/221,127, filed on Sep. 9, 2002, now abandoned, which is a continuation of application No. PCT/US01/07487, filed on Mar. 9, 2001.

(60) Provisional application No. 60/188,246, filed on Mar. 10, 2000.

(51) Int. Cl.
*A61F 2/44* (2006.01)

(52) U.S. Cl. .................. 623/17.11; 623/23.61

(58) Field of Classification Search ............... 623/17.11, 623/17.16, 23.51, 23.53, 23.54, 23.56, 23.61, 623/23.75; 606/246, 77, 151, 331
See application file for complete search history.

(56) References Cited

U.S. PATENT DOCUMENTS

| | | | |
|---|---|---|---|
| 3,824,631 A | 7/1974 | Burstein et al. | |
| 3,952,414 A | 4/1976 | Shovers et al. | |
| 4,222,128 A | 9/1980 | Tomonaga et al. | |
| 4,619,655 A | 10/1986 | Hanker et al. | |
| 4,963,151 A | 10/1990 | Ducheyne et al. | |
| 5,306,307 A | 4/1994 | Senter et al. | |
| 5,514,180 A * | 5/1996 | Heggeness et al. | 623/17.16 |
| 5,645,598 A | 7/1997 | Brosnahan, III | |
| 5,984,967 A | 11/1999 | Zdeblick et al. | |
| 6,086,613 A * | 7/2000 | Camino et al. | 623/17.16 |
| 6,294,187 B1 * | 9/2001 | Boyce et al. | 424/422 |
| 6,696,073 B2 | 2/2004 | Boyce et al. | |
| 2003/0014127 A1 | 1/2003 | Talja et al. | |
| 2004/0075192 A1 | 4/2004 | Boyer et al. | |

FOREIGN PATENT DOCUMENTS

WO WO 97/17285 * 5/1997

* cited by examiner

*Primary Examiner* — Eduardo C Robert
*Assistant Examiner* — David Comstock

(57) ABSTRACT

Interbody fusion implants that include a load bearing body composed of a calcium phosphate material hardened around one or more structural reinforcing members are provided. The reinforcing members aid the load bearing body in resisting bending forces and, in certain forms, aid in preventing expulsion of the implant after implantation. Methods for promoting fusion bone growth in the space between adjacent vertebrae and methods for making the inventive implants are also provided.

27 Claims, 7 Drawing Sheets

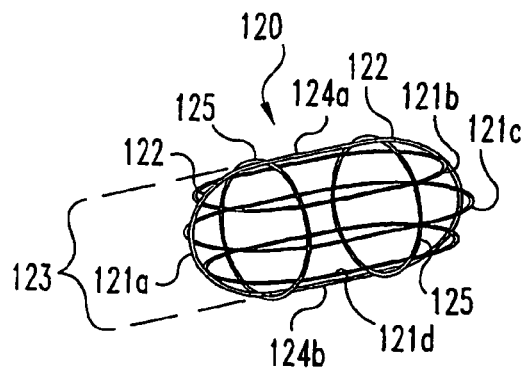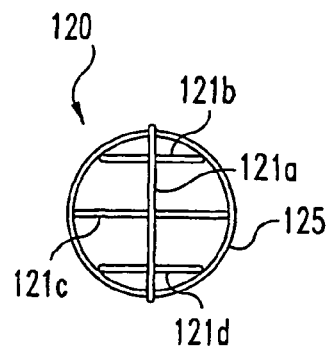
Fig. 17  Fig. 18
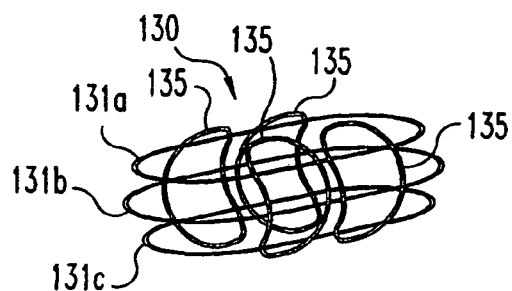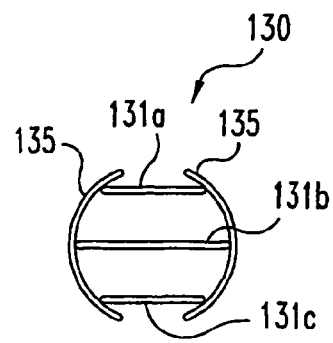
Fig. 19  Fig. 20
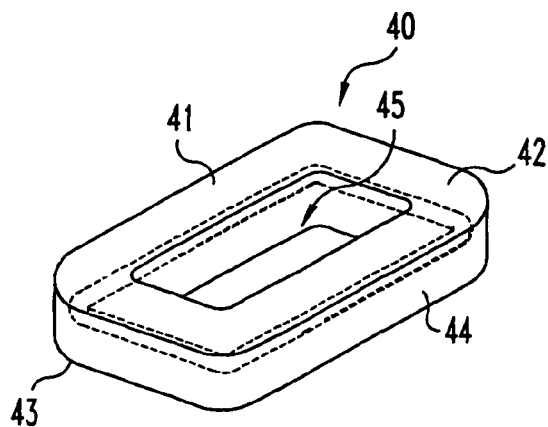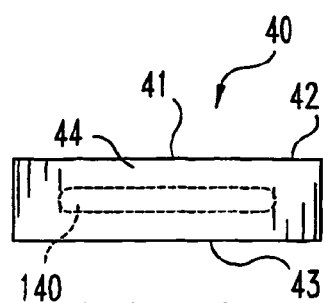
Fig. 21  Fig. 22

SYNTHETIC REINFORCED INTERBODY FUSION IMPLANTS

REFERENCE TO RELATED APPLICATIONS

The present application is a continuation of U.S. patent application Ser. No. 10/221,127, filed on Sep. 9, 2002, now abandoned which is a continuation of International Patent Application No. PCT/US01/07487 filed Mar. 9, 2001, designating the United States and published in English, which claims the benefit of U.S. Patent Application No. 60/188,246 filed Mar. 10, 2000, each of which is hereby incorporated by reference in its entirety.

BACKGROUND OF THE INVENTION

The present invention broadly concerns medical implants. More specifically, the invention provides reinforced interbody fusion implants and methods for making and using the implants.

Intervertebral discs, located between the endplates of adjacent vertebrae, stabilize the spine, distribute forces between vertebrae and cushion vertebral bodies. A normal intervertebral disc includes a semi-gelatinous component, the nucleus pulposus, which is surrounded and confined by an outer, fibrous ring called the annulus fibrosus. In a healthy, undamaged spine, the annulus fibrosus prevents the nucleus pulposus from protruding outside the disc space.

Spinal discs may be displaced or damaged due to trauma, disease or aging. Disruption of the annulus fibrosus allows the nucleus pulposus to protrude into the vertebral canal, a condition commonly referred to as a herniated or ruptured disc. The extruded nucleus pulposus may press on a spinal nerve, which may result in nerve damage, pain, numbness, muscle weakness and paralysis. Intervertebral discs may also deteriorate due to the normal aging process or disease. As a disc dehydrates and hardens, the disc space height will be reduced leading to instability of the spine, decreased mobility and pain.

Sometimes the only relief from the symptoms of these conditions is a discectomy, or surgical removal of a portion or all of an intervertebral disc followed by fusion of the adjacent vertebrae. The removal of the damaged or unhealthy disc will allow the disc space to collapse. Collapse of the disc space can cause instability of the spine, abnormal joint mechanics, premature development of arthritis or nerve damage, in addition to severe pain. Pain relief via discectomy and arthrodesis requires preservation of the disc space and eventual fusion of the affected motion segments.

Bone grafts are often used to fill the intervertebral space to prevent disc space collapse and promote fusion of the adjacent vertebrae across the disc space. In early techniques, bone material was simply disposed between the adjacent vertebrae, typically at the posterior aspect of the vertebra, and the spinal column was stabilized by way of a plate or rod spanning the affected vertebrae. Once fusion occurred, the hardware used to maintain the stability of the segment became superfluous and was a permanent foreign body. Moreover, the surgical procedures necessary to implant a rod or plate to stabilize the level during fusion were frequently lengthy and involved.

It was therefore determined that a more optimal solution to the stabilization of an excised disc space is to fuse the vertebrae between their respective end plates, preferably without the need for anterior or posterior plating. There have been an extensive number of attempts to develop an acceptable intradiscal implant that could be used to replace a damaged disc and maintain the stability of the disc interspace between the adjacent vertebrae, at least until complete artirodesis is achieved. The implant must provide temporary support and allow bone ingrowth. Success of the discectomy and fusion procedure requires the development of a contiguous growth of bone to create a solid mass because the implant may not withstand the compressive loads on the spine for the life of the patient.

There is a continuing need for interbody fusion implants which have sufficient strength to support the vertebral column until after the adjacent vertebrae are fused and which eliminate or at least minimize any permanent foreign body after the fusion.

SUMMARY OF THE INVENTION

In accordance with one aspect of the present invention, an implant includes a porous, biocompatible load bearing body composed of a synthetic calcium phosphate material that is hardened around at least one structural reinforcing member. The reinforcing member advantageously helps the load bearing body resist bending forces when implanted. The body is typically sized and configured for engagement between two vertebrae and has a superior surface configured to contact one vertebrae, and an inferior surface configured to contact another vertebrae. The reinforcing member is preferably an internal member and is disposed between the superior surface and inferior surface, extending along a length of the body.

In yet other embodiments, the implant includes a load bearing body composed of a hardened synthetic calcium phosphate material and at least one structural reinforcing member for resisting expulsion after implantation. The structural reinforcing member is at least partially embedded in the load bearing body and configured to contact adjacent vertebrae. The body is sized and configured for engagement between two vertebrae and has a superior surface and an inferior surface.

In yet another aspect of the invention, methods of promoting fusion bone growth between adjacent vertebrae are provided. In one form of the invention, a method includes providing an interbody fusion implant described above, preparing an adjacent vertebrae to receive the implant in an intervertebral space between adjacent vertebrae and placing the implant into the intervertebral space.

Other aspects of the invention provide methods for making the interbody fusion implants of the present invention. The preferred methods include providing a mold having positioned therein a structural reinforcing member, passing a hardenable synthetic calcium phosphate material into the mold, and causing the material to harden to form a load bearing implant.

These and other objects and advantages of the present invention will be apparent from the descriptions herein.

BRIEF DESCRIPTION OF THE FIGURES

FIG. 17 depicts a perspective view of an alternative embodiment of a reinforcing member.

FIG. 18 depicts an end view of the reinforcing member of FIG. 17.

FIG. 19 depicts a perspective view of an alternative embodiment of a reinforcing member.

FIG. 20 depicts an end view of the reinforcing member of FIG. 19.

FIG. 21 depicts a perspective view of a wedge-shaped interbody fusion implant.

FIG. 22 depicts an end view of the implant of FIG. 21.

DESCRIPTION OF THE PREFERRED EMBODIMENTS

For the purposes of promoting an understanding of the principles of the invention, reference will now be made to preferred embodiments and specific language will be used to describe the same. It will nevertheless be understood that no limitation of the scope of the invention is thereby intended, such alterations and further modifications of the invention, and such further applications of the principles of the invention as illustrated herein, being contemplated as would normally occur to one skilled in the art to which the invention relates.

As disclosed above, the present invention relates generally to synthetic reinforced medical implants. One specific aspect of the invention provides interbody fusion implants that include a porous, biocompatible load bearing body formed of a synthetic calcium phosphate material hardened around at least one internal reinforcing member for resisting bending or tensile forces when implanted. The implant may include a low crystallinity calcium phosphate material that is self-hardening, and requires no externally applied heat or pressure to harden, formed around a metallic reinforcing member, such as a metallic mesh. In alternative embodiments, the material is hardenable upon exposure to pressure and/or a temperature of about 5° C. to about 50° C., typically about 20° C. to 40° C.

Such implants are advantageous, for example, in minimizing the metal artifact in computer tomography (CT) or magnetic resonance imaging (MRI) which makes post-operative complications diagnosis easier. It is also easier to assess the fusion radiographically. Moreover, the above calcium phosphate materials may degrade over time and be replaced by bone. In addition, such implants may be constructed to provide for the relative absence of stress shielding, and make it easier to assess the fusion after the ceramic has degraded. Additionally, direct bone apposition to the calcium phosphate instead of possible fibrous tissue interfaces with metal devices is advantageous.

Figure 1:
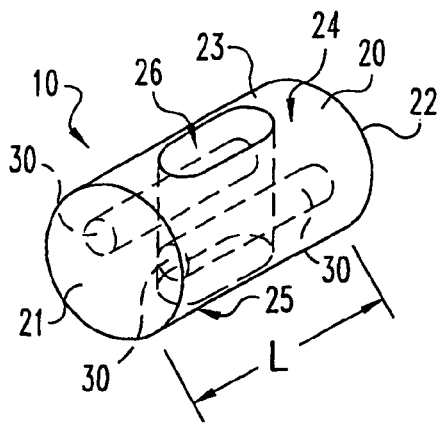
FIG. 1 depicts a perspective view of one embodiment of an interbody fusion implant.
Figure 2:
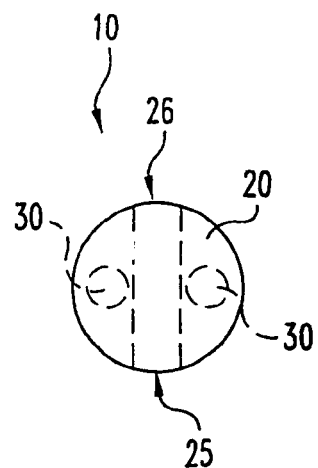
FIG. 2 depicts an end view of the implant of FIG. 1.
Figure 3:
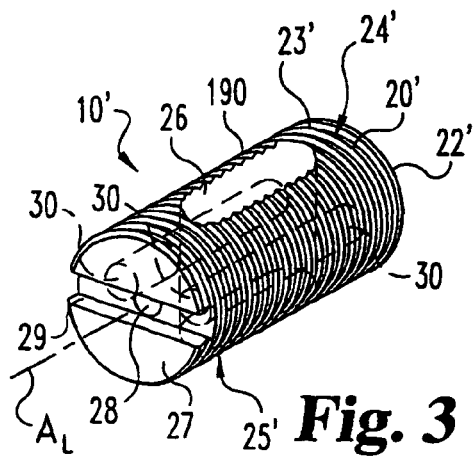
FIG. 3 depicts a perspective view of an alternative embodiment of the interbody fusion implant of the present invention.
Figure 4:
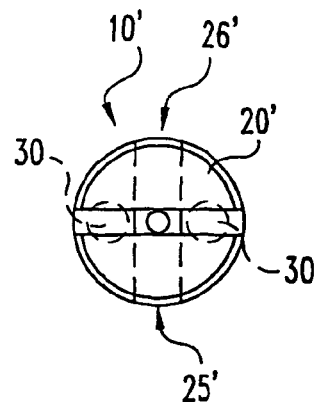
FIG. 4 depicts an end view of the implant of FIG. 3.

Referring now to FIGS. 1-5, an implant 10 may include a load bearing body 20 having disposed therein structural reinforcing members 30. Load bearing body 20 has a first end 21, a second end 22, and a wall 23 connecting first end 21 and second end 22. Wall 23 defines a first, superior surface 24 and a second, inferior surface 25 that are configured to contact adjacent vertebrae. Load bearing body 20 may optionally include a thru-hole 26 that may be filled with osteogenic material as further described below. Other configurations will be apparent to the skilled artisan. For example, in other embodiments, the hole may not extend completely through the load bearing body. The load bearing body may define a cavity, or other discontinuity on the superior and/or inferior surface that may also be advantageously filled with osteogenic material. The load bearing body may further include a tool-engagement end 27 that defines a tool engaging, or instrument attachment hole 28 as seen in FIGS. 3 and 4, wherein body 20' also includes a second end 22', a wall 23', a superior surface 24' and an inferior surface 25'. The body may further include a score 29, as seen in FIGS. 3 and 4, for indicating the orientation of other components of the implant 10, for example the hole 26 and/or the reinforcing members 30, as well as external threads 190.

Load bearing body 20 is preferably formed of a hardenable calcium phosphate material. A wide variety of calcium phosphate materials may be used including hydroxyapatite, tricalcium phosphate and mixtures thereof. The calcium phosphate material of which the load bearing body is composed preferably has a composition substantially similar to natural bone. Furthermore, a preferred synthetic calcium phosphate material is one that is flowable at a low temperature, such as below about 50° C., especially room temperature (about 25° C.), and is hardenable at such temperatures. More preferred materials will be flowable at room temperature (about 25° C.) and hardenable at about body temperature (about 37° C.). Such synthetic calcium phosphate materials include a poorly or low crystalline calcium phosphate, such as a low or poorly crystalline apatite, including hydroxyapatite, available from Etex Corporation and as described in U.S. Pat. Nos. 5,783,217; 5,676,976; 5,683,461; and 5,650,176, and PCT International Publication Nos. WO 98/16268, WO 96/39202 and WO 98/16209, all to Lee et al. As defined in the recited patents and herein, by "poorly or low crystalline" calcium phosphate material is meant a material that is amorphous, having little or no long range order and/or a material that is nanocrystalline ehhibiting crystalline domains on the order of nanometers or Angstroms. The calcium:phosphate ratio of the load bearing body is typically in the range of about 1.3 to 1.7, more typically about 1.5 to 1.7.

Other additives may be included in the compositions that form the load bearing bodies of the present invention to adjust their properties, including supporting or strengthening filler materials, pore forming agents and osteoinductive factors as described below.

As discussed above, and as seen in FIGS. 1-5, implant 10 includes at least one structural reinforcing member 30 disposed therein. FIGS. 1-4 depict two structural reinforcing members 30 disposed along the length of implant 10. The calcium phosphate material is preferably hardened around structural reinforcing members 30, such that the reinforcing members are contained within the load bearing body. Although the members shown in FIGS. 1-4 are completely surrounded by the load bearing body, they may, in alternative embodiments, be partially exposed.

The reinforcing members may be disposed between the superior surface and the inferior surface, and may extend along a length, of the load bearing body, including extending non-parallel, such as obliquely or transverse, or parallel to the superior and inferior surfaces of the body. Additionally, the reinforcing members may extend non-parallel, including obliquely or transverse, and in other forms may extend parallel, to the central longitudinal axis of the load bearing body of the implants.

Figure 5:
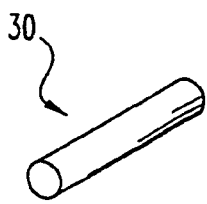
FIG. 5 depicts a perspective view of a structural reinforcing member used to reinforce the implant of FIG. 1.

Structural reinforcing members 30 may assume a wide variety of shapes. For example, member 30 may be cylindrical-shaped as best seen in FIG. 5. Member 30 may assume other shapes known in the art, including spherical, pyramidal, rectangular and other polygonal shapes. FIGS. 6-16 depict a variety of other ways in which the structural members may be configured.

Figure 6:
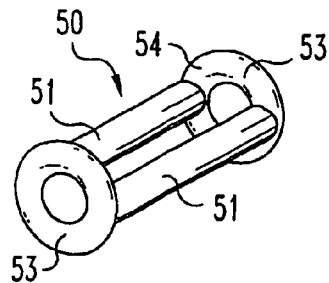
FIG. 6 depicts a perspective view of an alternative embodiment of a reinforcing member.
Figure 7:
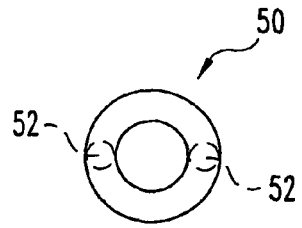
FIG. 7 depicts an end view of the reinforcing member of FIG. 7.

FIGS. 6 and 7 depict a structural member 50 having two longitudinal members 51 connected at either end 52 to end members 53. Each end 52 of longitudinal members 51 is attached to an internal surface 54 of end members 53. Longitudinal members 51 are preferably elongated members, such as cylindrical-shaped members, and are further preferably positioned generally parallel to each other. Longitudinal members 51 and end members 53 may be constructed independently and then joined by methods known to the art, or may be made as a single, integral unit or by any other variation known to the skilled artisan.

Figure 8:
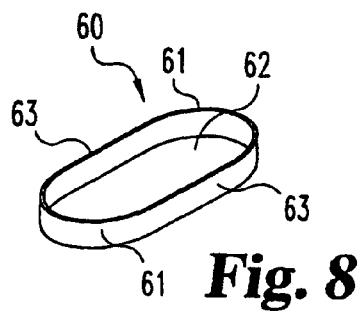
FIG. 8 depicts a perspective view of an alternative embodiment of a reinforcing member.
Figure 9:
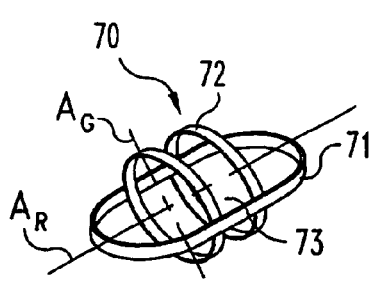
FIG. 9 depicts a perspective view of an alternative embodiment of a reinforcing member.
Figure 10:
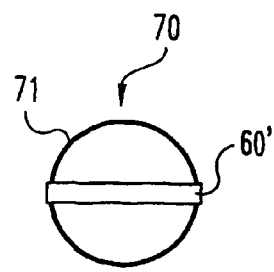
FIG. 10 depicts an end view of the reinforcing member of FIG. 9.

Referring now to FIG. 8, a reinforcing band member 60 is shown that is preferably a length of material that has been formed into a substantially ovate shape with rounded ends 61, sides 63 and defining a gap 62. The dimensions of reinforcing member 60, as with all the reinforcing members described herein, are such that will reinforce the load bearing body against bending forces. Such bending forces imposed upon the implant in situ include, for example, tensile forces and compressive forces. Referring now to FIG. 9, a reinforcing member 70 may include a reinforcing band 71 and attached intermediate-members 72 to form reinforcing member 70. Intermediate members 72 span the area, or gap 73 defined by reinforcing band 71 to form reinforcing member 70, and are positioned preferably such that a longitudinal axis $A_G$ of the intermediate members 72 is perpendicular to the longitudinal axis $A_R$ of reinforcing member 71 as seen in FIGS. 9 and 10. Two intermediate members 72 are seen in FIG. 9, although less than or more than this number may be present in order to affect the structural integrity of the load bearing body into which it is incorporated. Intermediate members 72 shown in FIGS. 9 and 10 are ring-shaped structures, but may also assume other shapes known in the art as described above.

Figure 11:
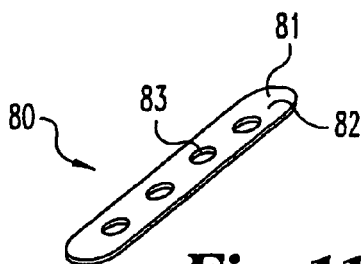
FIG. 11 depicts a perspective view of an alternative embodiment of a reinforcing member.

Referring now to FIG. 11, reinforcing member 80 is shown. Reinforcing member 80 is an elongated plate 81 having an outer surface 82. Plate 81 may further include thru-holes 83 disposed along the length of plate 81. One or more of reinforcing member 80 may be disposed within a particular load bearing body.

Figure 12:
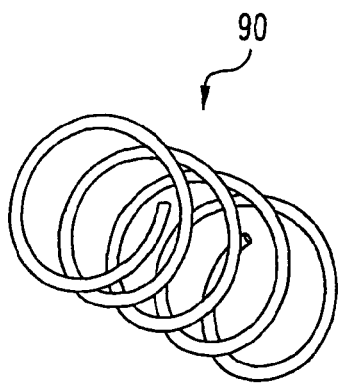
FIG. 12 depicts a perspective view of a helical-shaped reinforcing member.

Referring now to FIG. 12, a reinforcing member 90 shaped in a spiral, or helical configuration is shown. This particular configuration is advantageous in that, in one preferred form of the invention, reinforcing member 90 may be only partially embedded in the load bearing body such that it forms threads on the outer surface of the body as more fully described below.

The reinforcing members, or scaffolds, described herein may be made of a wide variety of materials that resist bending or tensile loads. Such materials will therefore increase the structural integrity of the load bearing bodies described herein. The reinforcing member is preferably formed of a metallic material, including titanium, stainless steel, tantalum and alloys thereof, as well as cobalt-chromium, cobalt-chromium-nickel and cobalt-chromium-molybdenum alloys. The reinforcing member may also be formed of other materials, for example, carbon fiber, carbon fiber composites, collagen strands (e.g. fibers or woven ropes), or plastics such as polyethylene, Dacron®, and degradable polymers. The reinforcing member will advantageously be combined with the load-bearing body to form an implant able to withstand compressive forces of at least about 40 MPa.

In one preferred embodiment of the present invention, the reinforcing members described above are composed of a mesh, such as a titanium mesh. The mesh may be formed into a reinforcing member that will form the shaped members described above. For example, metallic mesh may be shaped into several configurations that will form the cylindrical-shaped reinforcing members described in FIGS. 5 and 6. Still further alternative reinforcing members are shown in FIGS. 17-24, discussed more fully below.

Figure 13:
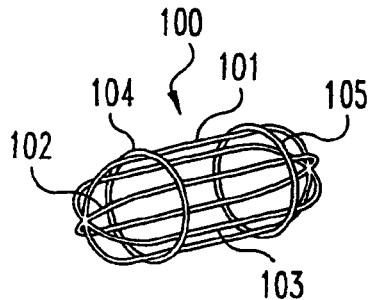
FIG. 13 depicts a perspective view of an alternative embodiment of a reinforcing member.
Figure 14:
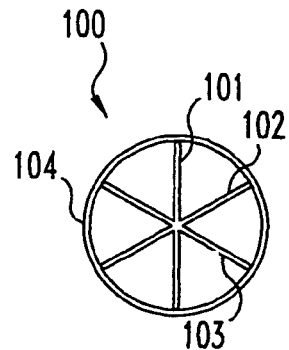
FIG. 14 depicts an end view of the reinforcing member of FIG. 13.

Referring now to FIGS. 13 and 14, reinforcing member 100 includes three generally ovate rings 101, 102 and 103 which are attached at their ends to form an overall, generally cylindrical shape. Reinforcing member 100 also includes end rings 104 and 105 to which ovate rings 101, 102 and 103 are attached at points of intersection to provide additional stability to the reinforcement member 100.

Figure 15:
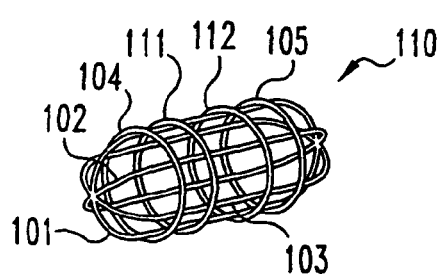
FIG. 15 depicts a perspective view of an alternative embodiment of a reinforcing member.
Figure 16:
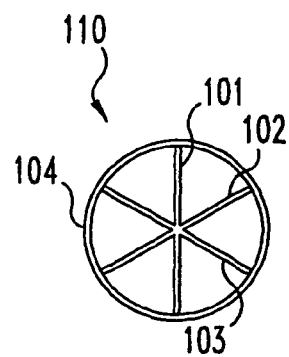
FIG. 16 depicts an end view of the reinforcing member of FIG. 15.

Referring now to FIGS. 15 and 16, reinforcing member 110 is shown and is identical to reinforcing member 100 except for the presence of attached intermediate rings 111 and 112 along the length of the ovate rings to provide still further stability.

Referring now to FIGS. 17 and 18, reinforcing member 120 includes a central wire 121a having an ovate shape with rounded ends 122, sides 124a and 124b and defining a gap, or area 123. Three additional ovate wire members, identified as upper wire 121b, medial wire 121c and lower wire 121d are disposed along the length of central wire 121a, and may be positioned one on top of each other, between sides 124a and 124b, such that a longitudinal plane passing independently through of each of the upper, medial and lower wires is non-parallel, e.g. perpendicular, to a similar longitudinal plane passing through central wire 121a, although other configurations are also envisioned. Reinforcing member 120 further includes wire stabilizer rings 125 connected to wires 121a-121d at intersecting locations.

Referring now to FIGS. 19 and 20, reinforcing member 130 is shown that includes upper, medial and lower wires 131a, 131b and 131c, respectively, disposed in the same configuration as shown for reinforcing member 120. Reinforcing member 130 includes end stabilizers 135 disposed about and connected at intersecting points to wires 131a-131c. End stabilizers 135 are preferably formed from a ring-shaped wire that is bent such that the profile of the ring-shaped wire is arcuate as best seen in the end view of reinforcing member 130 shown in FIG. 20.

Referring now to FIGS. 21 and 22, implant 40 includes a load bearing body 41 that is substantially rectangular in shape, and includes a first, superior surface 42, a second, inferior surface 43, and a wall 44 connecting the two surfaces. Wall 44 is preferably of a height approximating that of an intervertebral disc space of a mammal, such as a human. Load bearing body 41 may further define a thru-hole 45 into which osteogenic material may be disposed. In alternative embodiments, load bearing body may define a cavity or other discontinuity on superior surface 42 and/or inferior surface 43 into which osteogenic material may be disposed. Reinforcing member 140 is disposed within load bearing body 40.

Figure 23:
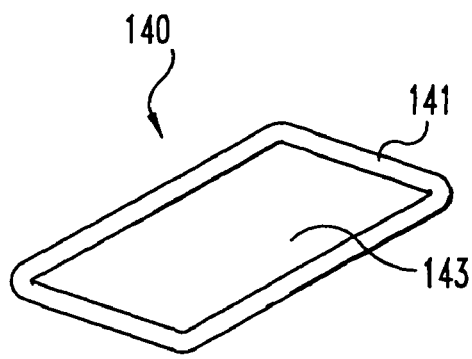
FIG. 23 depicts a reinforcing member that may reinforce the wedge-shaped implant of FIG. 25.

Reinforcing member 140 for load bearing body 40 is depicted separately in FIG. 23. Reinforcing member 140 includes a body 141 that is also substantially rectangular-shaped and defines a gap 143 to provide an opening corresponding to the location of thru-hole 45 of implant 40 (see FIG. 21).

Figure 24:
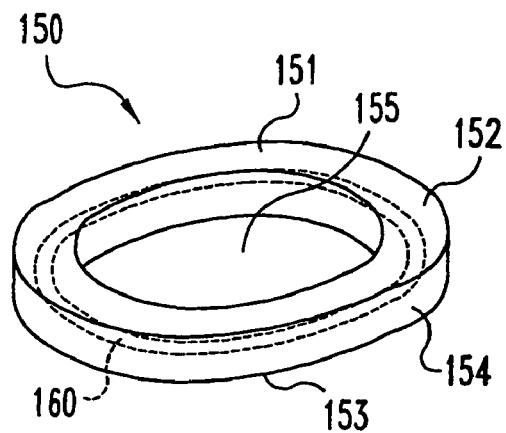
FIG. 24 depicts a perspective view of an elliptical-shaped interbody fusion implant.
Figure 25:
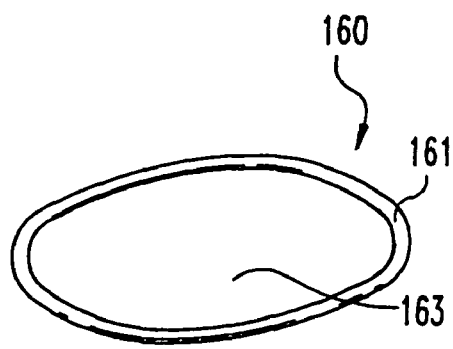
FIG. 25 depicts a perspective view of the reinforcing member of the implant of FIG. 24.

Yet another example of an implant configuration of the present invention is shown in FIGS. 24 and 25. Implant 150 is shown including load bearing body 151 that is substantially elliptical in shape, and includes a first, superior surface 152, a second, inferior surface 153 and a wall 154 connecting first surface 152 and second surface 153. Load bearing body 151 may also include a thru-hole 155 or other area which may be used for containing osteogenic material therein as discussed above. Internal structural reinforcing member 160 is disposed within load bearing body 151. As seen in FIG. 25, reinforcing member 160 includes a body 161 that is substantially elliptical in shape and defines a gap 163 to provide an opening corresponding to the location of thru-hole 155 of implant 150.

As mentioned above, the thru-holes or other apertures or discontinuities may be filled with an osteogenic material. Any suitable osteogenic material or composition is contemplated, including autograft, allograft, xenograft, demineralized bone, synthetic and natural bone graft substitutes, such as bioceramics, polymers, and osteoinductive factors. The terms osteogenic material or osteogenic composition as used herein mean virtually any material that promotes bone growth or healing including autograft, allograft, xenograft, bone graft substitutes and natural, synthetic and recombinant proteins, nucleotide sequences (e.g. genes such as growth factor genes), hormones and the like.

Autograft can be harvested from locations such as the iliac crest using drills, gouges, curettes, trephines and other tools and methods which are well known to surgeons in this field. Preferably, autograft is harvested from the iliac crest with minimally invasive surgery. The osteogenic material may also include bone reamed away by the surgeon while preparing the end plates for the implant.

Advantageously, where autograft is chosen as the osteogenic material, only a very small amount of bone material is needed to pack the thru-hole. The autograft itself is not required to provide structural support as this is provided by the implant. The donor surgery for such a small amount of bone is less invasive and better tolerated by the patient. There is usually little need for muscle dissection in obtaining such small amounts of bone. The present invention therefore eliminates or minimizes many of the disadvantages of employing autograft.

Natural and synthetic graft substitutes which replace the structure or function of bone are also contemplated for the osteogenic composition. Any such graft substitute is contemplated, including for example, demineralized bone matrix, mineral compositions and bioceramics. As is evident from a review of *An Introduction to Bioceramnics*, edited by Larry L. Hench and June Wilson (World Scientific Publishing Co. Ptd. Ltd, 1993, volume 1), there is a vast array of bioceramic materials, including BIOGLASS®, hydroxyapatite and calcium phosphate compositions known in the art which can be used to advantage for this purpose. This disclosure is herein incorporated by reference for this purpose. Preferred compositions include bioactive glasses, tricalcium phosphates and hydroxyapatites. In one embodiment, the graft substitute is a biphasic calcium phosphate ceramic including tricalcium phosphate and hydroxyapatite.

In some embodiments, the osteogenic compositions used in this invention comprise a therapeutically effective amount to stimulate or induce bone growth of a substantially pure bone inductive or growth factor or protein in a pharmaceutically acceptable carrier. The preferred osteoinductive factors are the recombinant human bone morphogenetic proteins (rhBMPs) because they are available in unlimited supply and do not transmit infectious diseases. Most preferably, the bone morphogenetic protein is a rhBMP-2, rhBMP-4, rhBMP-7, or heterodimers thereof.

Recombinant BMP-2 can be used at a concentration of about 0.4 mg/ml to about 1.5 mg/ml, preferably near 1.5 mg/ml. However, any bone morphogenetic protein is contemplated including bone morphogenetic proteins designated as BMP-1 through BMP-18. BMPs are available from Genetics Institute, Inc., Cambridge, Mass. and the BMPs and genes encoding them may also be prepared by one skilled in the art as described in U.S. Pat. No. 5,187,076 to Wozney et al.; U.S. Pat. No. 5,366,875 to Wozney et al.; U.S. Pat. No. 4,877,864 to Wang et al.; U.S. Pat. No. 5,108,922 to Wang et al.; U.S. Pat. No. 5,116,738 to Wang et al.; U.S. Pat. No. 5,013,649 to Wang et al.; U.S. Pat. No. 5,106,748 to Wozney et al.; and PCT Patent Nos. WO93/00432 to Wozney et al.; WO94/26893 to Celeste et al.; and WO94/26892 to Celeste et al. All osteoinductive factors are contemplated whether obtained as above or isolated from bone. Methods for isolating bone morphogenetic protein from bone are described, for example, in U.S. Pat. No. 4,294,753 to Urist and Urist et al., 81 PNAS 371, 1984.

The choice of carrier material for the osteogenic composition is based on biocompatibility, biodegradability, mechanical properties and interface properties as well as the structure of the load bearing member. The particular application of the compositions of the invention will define the appropriate formulation. Potential carriers include calcium sulphates, polylactic acids, polyanhydrides, collagen, calcium phosphates, hyaluronic acid, polymeric acrylic esters and demineralized bone. The carrier may be any suitable carrier capable of delivering the proteins, nucleotide sequences, or the like. Most preferably, the carrier is capable of being eventually resorbed into the body. One preferred carrier is an absorbable collagen sponge marketed by Integra LifeSciences Corporation under the trade name Helistat® Absorbable Collagen Hemostatic Agent. Another preferred carrier is a biphasic calcium phosphate ceramic. Ceramic blocks and granules are commercially available from Sofamor Danek Group, B. P. 4-62180 Rang-du-Fliers, France and Bioland, 132 Rou d Espangne, 31100 Toulouse, France. The osteoinductive factor is introduced into the carrier in any suitable manner. For example, the carrier may be soaked in a solution containing the factor.

In many cases, the osteoinductive factor may be included in the calcium phosphate material prior to its hardening around the reinforcing member to form the interbody fusion implant as the hardening typically is performed at or below 37° C. Alternatively, the factor, such as a bone morphogenetic protein in a suitable liquid carrier, may be applied onto and/or into the hardened, porous load bearing body after hardening, for instance by soaking, dripping, etc.

The interbody fusion implants of the invention may be provided with surface features defined in their outer surfaces. In one form of the invention, for example, at least one of the ends of the implant is a tool engagement end 27 that defines a tool engaging or instrument attachment hole 28 as seen in FIGS. 3 and 4. In a preferred embodiment, hole 28 is threaded but any suitable attachment configuration is contemplated.

Figure 26:
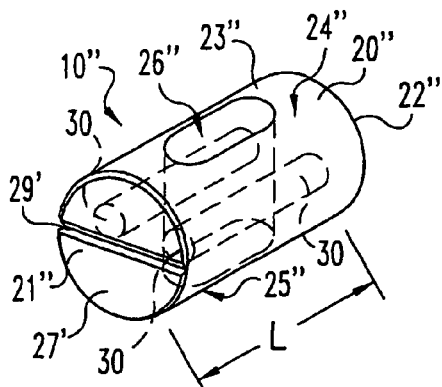
FIG. 26 depicts a perspective view of an alternative embodiment of the interbody fusion implant of the present invention, having a score mark in one end.

Interbody fusion implants of the present invention may further include a tool-engaging slot 29 for receiving an implantation tool. The slot is typically perpendicular to the central longitudinal axis $A_L$ of the implant, as shown, for example, in FIG. 3. In yet other embodiments, the slot 29 may serve as an alignment score mark or groove 29' defined in tool engagement end 27' of implant 10" seen in FIG. 26, thus making the opposite end the insertion end. Implant 10" is identical in all respects to implant 10', except for the difference in the feature present on an end of the implant and the absence of external threads. Thus, components of spacer 10" are numbered correspondingly to those of spacer 10', except with a denoting prime "'"" symbol.

Alternatively, a projection may be formed on the end walls instead of a slot. Such a projection may form a straight, flat-sided shape (such as a mirror image of the slot depicted in FIG. 3), an elliptical eminence, a bi-concave eminence, a square eminence, or any other protruding shape which provides sufficient end-cap or tool engaging end strength and drive purchase to allow transmission of insertional torque without breaking or otherwise damaging the eminence.

Yet other surface features can be defined along the length L of the spacer. As mentioned above with respect to FIGS. 3 and 4, the outer surface of the implant may define threads 190 or other expulsion-resistant configurations such as teeth, grooves, waffle patterns, etc. The threads or other surface features may also stabilize the bone-spacer interface and reduce micromotion to facilitate fusion. The implants of the present invention may be provided with threads by methods well known to the skilled artisan such as incorporation of threaded features in a mold in which the load bearing body is hardened, and/or by matching the piece after hardening.

Figure 27:
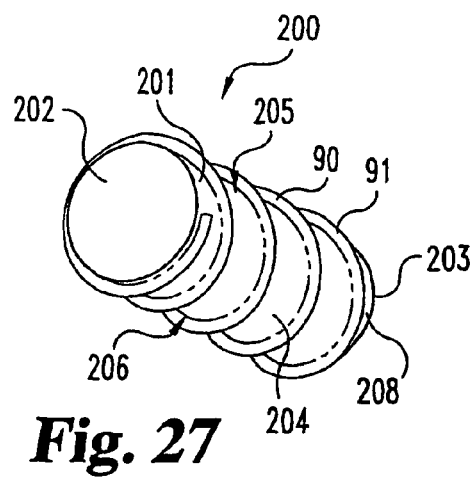
FIG. 27 depicts a perspective view of an alternative embodiment of an interbody fusion implant of the present invention, showing a load bearing body reinforced with a spiral reinforcing member that forms threads on the outer surface of the implant.
Figure 28:
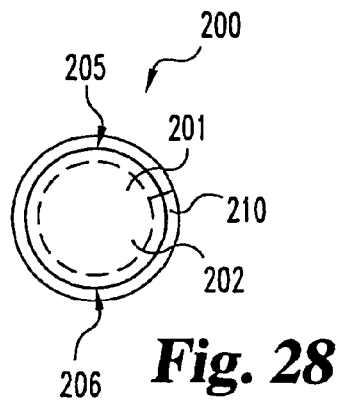
FIG. 28 depicts an end view of the implant of FIG. 27.

In certain embodiments, the threads or other expulsion-resistant surface features may be formed from the reinforcing members, as illustrated in FIGS. 27 and 28. Implant 200 includes a load bearing body 201 having disposed therein structural reinforcing member 90 which includes a body 91 which has a helical, or spiral, configuration. Load bearing body 201 further has a first end 202, a second end 203, and a wall 204 connecting first end 202 and second end 203. Wall 23 also defines a first, superior surface 205 and a second, inferior surface 206. Reinforcing member 90 is disposed in load bearing body 201 so that at least a portion of reinforcing member 90 is exposed from the outer surface of body 91 to form threads on outer surface 208 of implant 200. A substantial portion of reinforcing member 90 is embedded in load bearing body 201 to provide fixation of the member 90 within body 201 and preferably also to improve the resistance of implant 200 against bending forces.

Figure 29:
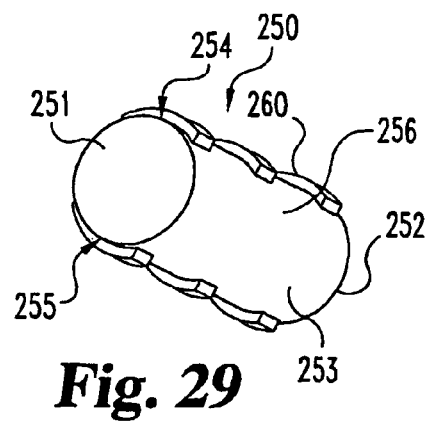
FIG. 29 depicts a perspective view of an alternative embodiment of an interbody fusion implant of the present invention.
Figure 30:
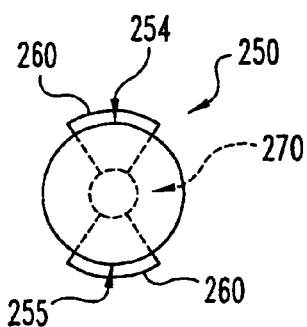
FIG. 30 depicts an end view of the implant of FIG. 29.
Figure 31:
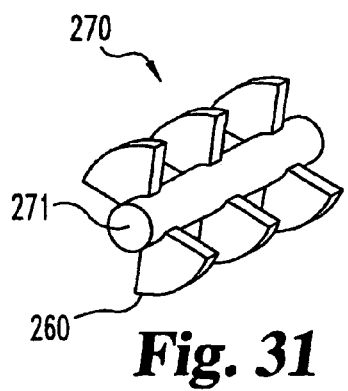
FIG. 31 depicts a perspective view of reinforcing member 270, with radially extending plates 260, that may be used to reinforce the implant of FIG. 30.

Referring now to FIGS. 29 and 30, an implant 250 is shown that includes plates that may provide reinforcement and further aid in preventing expulsion of the implant after implantation. Implant 250 includes a load bearing body 256 that has a first end 251, second end 252 and a wall 253 connecting first end 251 and second end 252. The illustrated implant includes an elongate reinforcing member 270 that is disposed, and preferably partially embedded, in load bearing body 256. Reinforcing member 270 includes body 271, extending along the central longitudinal axis of implant 250. Plates 260 extend radially from body 271 of reinforcing member 270, and are partially exposed on superior surface 254 and inferior surface 255 of implant 250 or are otherwise partially embedded in load bearing body 256. The plates 260 may be configured and positioned to resist expulsion of the implant after implantation. Reinforcing member 270, with radially extending plates 260, is best seen in FIG. 31.

Figure 32:
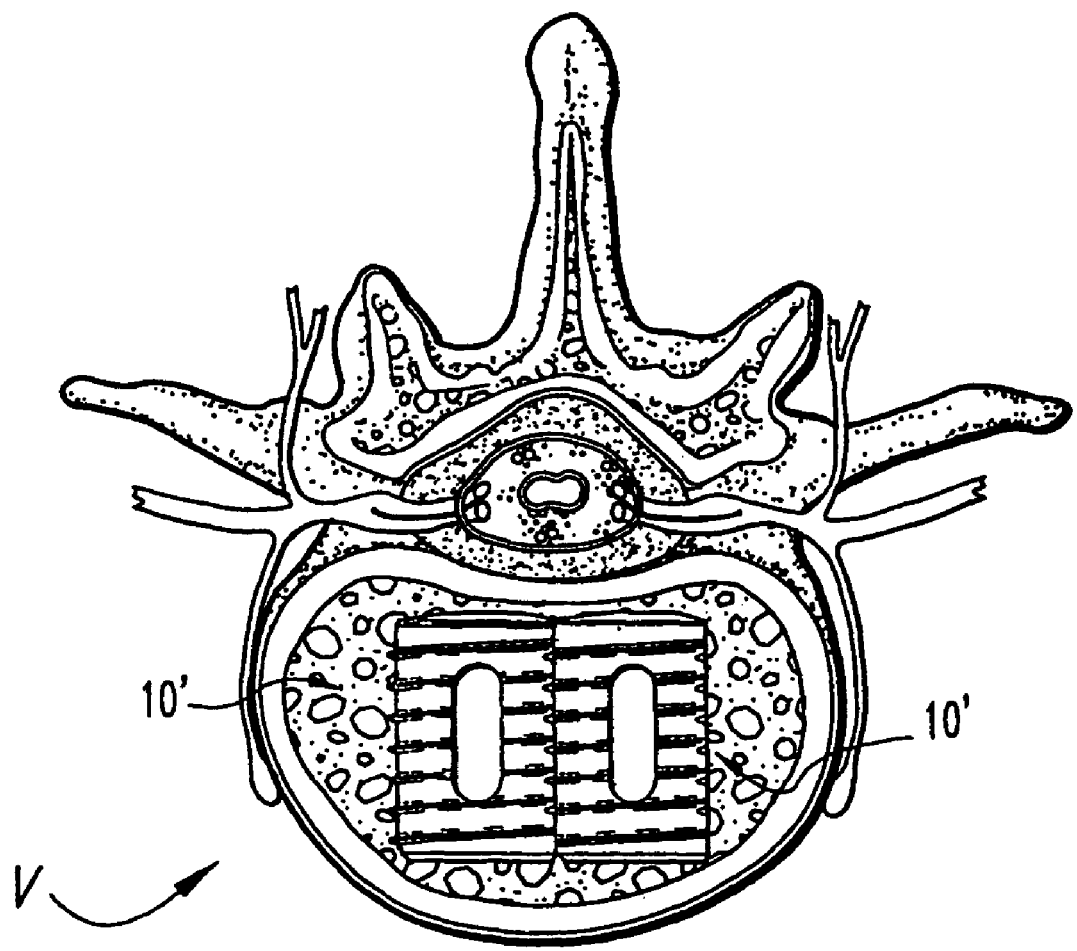
FIG. 32 depicts a top view of two implants of the present invention bilaterally implanted within an intervertebral space.

In yet another aspect of the present invention, methods of promoting fusion bone growth between adjacent vertebrae are provided. In one form of the invention, a method includes providing a first interbody fusion implant described herein, such as one having a load bearing body with a reinforcing member disposed therein. The implant selected is of the appropriate dimensions, based on the size of the cavity created and the needs of the particular patient undergoing the fusion. The adjacent vertebrae are prepared to receive the spacer in an intervertebral space between adjacent vertebrae according to conventional procedures. The spacer is mounted on an instrument known to the art, preferably via an instrument attachment hole. An osteogenic material may optionally be placed within a thin-hole, or gap, of the implant should one be present. The implant is then inserted into the cavity created between the adjacent vertebrae to be fused. Once the implant is properly oriented within the intervertebral space, the implant may be disengaged from the instrument. In a preferred form of the invention, a second implant is inserted into the intervertebral space after the first implant is properly positioned near vertebral body V, resulting in bilateral placement of the spacers as seen in FIG. 32. Osteogenic material may also optionally be placed within those implants having thru-holes.

In a further aspect of the present invention, methods of making an interbody fusion implant are provided. In one form of the invention, a method of making an interbody fusion implant includes providing a mold having positioned therein a structural reinforcing member. The mold will be shaped as desired to form an implant having the desired shape. The reinforcing member may include at least one of the reinforcing members, or similar members, described herein. A hardenable, flowable synthetic calcium phosphate material, for example selected from materials described above, is then poured or otherwise passed into the mold. The material is then caused to harden, by, for example, exposing the material to temperatures of 37° C. or below, and/or exposing the material to pressure.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected. In addition, all references cited herein are indicative of the level of skill in the art and are hereby incorporated by reference in their entirety.

What is claimed is:

1. An interbody fusion implant, comprising:
a biocompatible load bearing body, said body comprised of a synthetic calcium phosphate material hardened around at least one structural reinforcing member for resisting bending forces when implanted, said body having a longitudinal axis and being sized and configured for engagement between two vertebrae and having a superior surface configured to contact one of said vertebrae, and an inferior surface configured to contact the other of said vertebrae, said structural reinforcing member being a straight cylinder disposed between said superior surface and said inferior surface and extending along a length of said body parallel to and offset from said longitudinal axis.

2. The interbody fusion implant of claim 1, wherein said calcium phosphate ceramic is a calcium phosphate apatite.

3. The interbody fusion implant of claim 2, wherein said calcium phosphate apatite is a low crystallinity apatite.

4. The interbody fusion implant of claim 1, wherein said reinforcement member is comprised of a metal.

5. The interbody fusion implant of claim 4, wherein said metal is a titanium mesh.

6. The interbody fusion implant of claim 4, wherein said metal is selected from the group consisting of titanium, stainless steel, cobalt-chromium, tantalum, mixtures thereof and alloys thereof.

7. The interbody fusion implant of claim 1, wherein said implant has a compressive strength of at least about 40 MPa.

8. The interbody fusion implant of claim 1, wherein said body further comprises a tool engaging end defining a tool engaging hole for receiving a driving tool for implanting the spacer.

9. The interbody fusion implant of claim 1, wherein said body has an outer surface that defines threaded bone-engaging portions.

10. The interbody fusion implant of claim 1, wherein said implant is a dowel.

11. The interbody fusion implant of claim 1, wherein said implant is a wedge.

12. The interbody fusion implant of claim 1, wherein said body further includes a wall connecting said superior surface and said inferior surface.

13. The interbody fusion implant of claim 12, wherein said body is elliptical.

14. The interbody fusion implant of claim 1, wherein said body further defines at least one thru-hole, and said structural reinforcing member is parallel to and offset from said thru-hole.

15. The interbody fusion implant of claim 14, wherein said body has a longitudinal axis and said thru-hole extends perpendicular to said longitudinal axis.

16. The interbody fusion implant of claim 15, wherein said body further includes an osteogenic material disposed within said thru-hole.

17. The interbody fusion implant of claim 16, wherein said osteogenic material comprises natural bone, demineralized bone, a calcium phosphate material, a bioceramic, bioglass, an osteoinductive factor and mixtures thereof.

18. The interbody fusion implant of claim 17, wherein said osteoinductive factor comprises a bone morphogenetic protein.

19. The interbody fusion implant of claim 18, wherein said bone morphogenetic protein comprises a recombinant protein.

20. The interbody fusion implant of claim 19, wherein said recombinant bone morphogenetic protein comprises a human protein.

21. The interbody fusion implant of claim 20, wherein said recombinant human protein comprises BMP-2, BMP-4, BMP-7, or heterodimers thereof.

22. The interbody fusion implant of claim 1, wherein said reinforcing member extends parallel to said superior and inferior surfaces.

23. The interbody fusion implant of claim 1, wherein said reinforcing member further includes a second straight cylindrical member that is offset from and not intersecting said longitudinal axis, with said longitudinal axis lying between said straight cylindrical members.

24. An interbody fusion implant, comprising:
a load bearing body formed of a hardened synthetic calcium phosphate material and having a longitudinal axis, said body including at least one internal reinforcing member adapted to resist bending or tensile forces along a length of said body, said body sized and configured for engagement between two vertebrae and having a first surface for contacting a first of said vertebrae and a second surface for contacting another of said vertebrae, said body further having a hole extending between a first opening in said first surface and a second opening in said second surface and an axis parallel to the longitudinal axis of the body, said reinforcing member comprising at least one straight cylinder, said cylinder being offset from said hole and non-perpendicular to said hole axis.

25. An interbody fusion implant, comprising:
a cylindrical biocompatible load-bearing body, said body comprised of a synthetic calcium phosphate material hardened around first and second straight cylindrical structural reinforcing members for resisting bending forces when implanted, said body having a longitudinal axis and being sized and configured for engagement between two vertebrae and having a superior surface configured to contact one of said vertebrae, and an inferior surface configured to contact the other of said vertebrae, said structural reinforcing member being disposed between said superior surface and said inferior surface so that said structural reinforcing members are parallel or oblique with respect to said longitudinal axis and to each other, said structural reinforcing members being offset from said axis and separated from each other so that neither structural reinforcing member intersects said axis.

26. The apparatus of claim 25, wherein said body includes an opening extending through said superior surface and said inferior surface and along said longitudinal axis, with said structural reinforcing members being offset to the outside of said opening.

27. The apparatus of claim 25, wherein said structural reinforcing members are placed with respect to said longitudinal axis so that a perpendicular line can be drawn from said first structural reinforcing member to said second structural reinforcing member that intersects said longitudinal axis.

* * * * *